United States Patent
Marcolino Quintao Severgnini et al.

(10) Patent No.: US 12,023,132 B2
(45) Date of Patent: Jul. 2, 2024

(54) SYSTEMS AND METHODS FOR REMOTE VITAL SIGN MONITORING IN A VEHICLE

(71) Applicant: TOYOTA MOTOR ENGINEERING & MANUFACTURING NORTH AMERICA, INC., Plano, TX (US)

(72) Inventors: Frederico Marcolino Quintao Severgnini, Ann Arbor, MI (US); Ercan M. Dede, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 202 days.

(21) Appl. No.: 17/027,572

(22) Filed: Sep. 21, 2020

(65) Prior Publication Data

US 2022/0087540 A1    Mar. 24, 2022

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1126* (2013.01); *A61B 5/25* (2021.01); *A61B 5/6822* (2013.01); *A61B 5/6823* (2013.01); *A61B 5/6893* (2013.01); *A61B 5/721* (2013.01); *A61B 5/7267* (2013.01); *A61B 5/746* (2013.01); *B60R 11/00* (2013.01); *G06N 3/02* (2013.01); *G06N 20/00* (2019.01); *G16H 40/67* (2018.01);
(Continued)

(58) Field of Classification Search
CPC ....... A61B 5/0205; A61B 5/1126; A61B 5/25; A61B 5/6822; A61B 5/6823; A61B 5/6893; A61B 5/721; A61B 5/7267; A61B 5/746; A61B 5/02438; A61B 5/0816; A61B 2562/0219; B60R 11/00; G06N 3/02; G06N 20/00; G06N 3/08; G16H 40/67; G16H 50/20
See application file for complete search history.

(56) References Cited

U.S. PATENT DOCUMENTS 8,725,311 B1 *   5/2014  Breed .................. A61B 5/11
                                                                701/1
9,782,087 B2 *  10/2017  Yamaji ................ A61B 5/0507
(Continued)

FOREIGN PATENT DOCUMENTS

WO    2015174963 A1    11/2015

OTHER PUBLICATIONS

Malesevic, N.; Petrovic, V.; Belic, M.; Antfolk, C.; Mihajlovic, V.; Jankovic, M., Contactless Real-Time Heartbeat Detection via 24 GHz Continuous-Wave Doppler Radar Using Artificial Neural Networks, Sensors 2020, 20, 2351, pp. 1-16.
(Continued)

*Primary Examiner* — Rufus C Point
(74) *Attorney, Agent, or Firm* — Haynes and Boone, LLP (57) ABSTRACT

Apparatuses and methods for monitoring vital signs. Movement data for a selected body location of a person in a vehicle is generated using a movement sensor positioned remotely with respect to the person. Input data is formed for a machine learning system using the movement data. The input data is processed using the machine learning system to remove noise from the input data and generate a target output that identifies a vital sign of the person.

20 Claims, 8 Drawing Sheets

(51) Int. Cl.

| | |
|---|---|
| *A61B 5/024* | (2006.01) |
| *A61B 5/08* | (2006.01) |
| *A61B 5/11* | (2006.01) |
| *A61B 5/25* | (2021.01) |
| *B60R 11/00* | (2006.01) |
| *G06N 3/02* | (2006.01) |
| *G06N 20/00* | (2019.01) |
| *G16H 40/67* | (2018.01) |

(52) U.S. Cl.
CPC ......... *A61B 5/02438* (2013.01); *A61B 5/0816* (2013.01); *A61B 2562/0219* (2013.01)

(56) References Cited

U.S. PATENT DOCUMENTS

| | | | | |
|---|---|---|---|---|
| 10,427,645 | B2 | 10/2019 | Karandikar et al. | |
| 10,688,867 | B2* | 6/2020 | Wilson | G08B 25/016 |
| 2008/0234899 | A1 | 9/2008 | Breed et al. | |
| 2009/0179390 | A1* | 7/2009 | Wurmthaler | B60N 2/501 |
| | | | | 280/5.519 |
| 2010/0070132 | A1* | 3/2010 | Doi | B62K 11/007 |
| | | | | 701/124 |
| 2010/0321572 | A1* | 12/2010 | Cornett | H04N 7/002 |
| | | | | 348/739 |
| 2012/0023049 | A1* | 1/2012 | Doerr | A61B 5/7264 |
| | | | | 706/20 |
| 2014/0058254 | A1* | 2/2014 | Yamaji | A61B 5/0507 |
| | | | | 600/430 |
| 2014/0135598 | A1* | 5/2014 | Weidl | G16H 40/63 |
| | | | | 600/300 |
| 2015/0286952 | A1* | 10/2015 | El Dokor | G06N 20/00 |
| | | | | 701/1 |
| 2016/0001781 | A1* | 1/2016 | Fung | G16H 50/20 |
| | | | | 701/36 |
| 2018/0122073 | A1 | 5/2018 | Holger | |
| 2018/0186234 | A1* | 7/2018 | Mestha | A61B 5/18 |
| 2018/0348759 | A1* | 12/2018 | Freeman | A61N 1/3904 |
| 2019/0332902 | A1* | 10/2019 | Gallagher | G06K 9/6293 |
| 2019/0382025 | A1* | 12/2019 | Mena Benito | A61B 5/0077 |
| 2020/0383580 | A1* | 12/2020 | Shouldice | A61B 5/02416 |

OTHER PUBLICATIONS

Yang, Z.; Bocca, M.; Jain V.; Mohapatra, P., Contactless Breathing Rate Monitoring in Vehicle Using UWB Radar. RealWSN'18: Proceedings of the 7th International Workshop on Real-World Embedded Wireless Systems and Networks, Nov. 2018, pp. 13-18. https://doi.org/10.1145/3277883.3277884.

Leonhardt, S.; Leicht, L.; Teichmann, D., Unobtrusive Vital Sign Monitoring in Automotive Environments—A Review, Sensors 2018, 18, 3080; doi: 10.3390/s18093080, pp. 1-38. www.mdpi.com/journal/sensors.

Binah AI, Contactless, Video-based Vital Signs Monitoring, https://www.binah.ai/wp-content/uploads/2019/10/Binah.ai_DigitalHealthcare_NOV2019_WEB-1.pdf.

Ambrosanio, M.; Franceschini S; Grassini, G.; Baselice, F.; A Multi-Channel Ultrasound System for Non-Contact Heart Rate Monitoring, in IEEE Sensors Journal, vol. 20, No. 4, pp. 2064-2074, 15 Feb.15, 2020, doi: 10.1109/JSEN.2019.2949435.

Mercuri, M., Lorato, I.R., Liu, YH. et al. Vital-sign monitoring and spatial tracking of multiple people using a contactless radar-based sensor. Nature Electronics 2, 252-262 (2019). https://doi.org/10.1038/s41928-019-0258-6.

Cosoli G. et al., Evaluation of Heart Rate Variability by means of Laser Doppler Vibrometry measurements, 2015 J. Phys.: Conf. Ser. 658 (2015) 012002.

Kwon, Jihoon; Kwak, Nojun, Human detection by neural networks using a low-cost short-range Doppler Radar Sensor, 6 pages, publication date unknown.

* cited by examiner

SYSTEMS AND METHODS FOR REMOTE VITAL SIGN MONITORING IN A VEHICLE

FIELD

The present disclosure relates generally to monitoring vital signs and, more particularly, to systems and methods for remote vital sign monitoring inside a vehicle using a machine learning system.

BACKGROUND

Many commercially available technologies for monitoring vital signs rely on contact-based sensors. In other words, these technologies rely on sensors that need to be placed in contact with the user whose vital signs are being monitored. As one example, one type of available wearable device uses contact to measure heart rate via photoplethysmography. Electrocardiogram (ECG) electrodes that are placed in contact with skin can also be used to measure heart rate. Wearable respiration belts may be used to measure respiration rate. Using such contact-based or wearable sensors in a vehicle, however, may be difficult because such sensors may be cumbersome or uncomfortable for the user while driving or riding in the vehicle.

Some currently available technologies for measuring vital signs in a contact-free manner rely on measuring skin displacement. For example, a laser vibrometer may be used to measure skin displacement in the sub-millimeter (sub-mm) range for use in determining heart rate based on chest expansion. These types of contactless technologies, however, are vulnerable to vibrations in the environment. Vehicles experience various vibrations during travel due to road conditions, vehicle speed, weather conditions, and other such factors. Thus, these types of conventional contactless technologies may be unable to provide accurate data in such a vehicle environment.

SUMMARY

In one example embodiment, a system comprises a movement sensor and a vital sign manager. The movement sensor is positioned in a vehicle remotely with respect to a person in the vehicle for generating movement data for a selected body location of the person. The vital sign manager forms input data for a machine learning system using the movement data and processes the input data using the machine learning system to remove noise from the input data and generate a target output that identifies a vital sign of the person.

In another example embodiment, movement data for a selected body location of a person in a vehicle is generated using a movement sensor positioned in the vehicle remotely with respect to the person. Input data is formed for a machine learning system using the movement data. The input data is processed using the machine learning system to remove noise from the input data and generate a target output that identifies a vital sign of the person.

In yet another example embodiment, a method is provided that includes receiving training data collected for a set of training scenarios. The training data includes measured vital sign data and sensor training data. The sensor training data includes surface displacement data that is generated remotely with respect to at least one person. Input data for a neural network system is formed using the sensor training data. The neural network system is trained using the input data to remove noise and generate a target output that corresponds with the measured vital sign data.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals, letters, or both in the various examples. This repetition is for the purpose of simplicity and clarity and does not in itself dictate a relationship between the various embodiments and/or configurations discussed.

DETAILED DESCRIPTION

Illustrative embodiments and related methods of the present disclosure are described below as they might be employed in one or more methods and systems for monitoring vital signs in a vehicle. In the interest of clarity, not all features of an actual implementation or method are described in this specification. It will of course be appreciated that in the development of any such actual embodiment, numerous implementation specific decisions must be made to achieve the developers' specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further aspects and advantages of the various embodiments and related methods of the disclosure will become apparent from consideration of the following description and drawings.

The example embodiments described below recognize that it may be desirable to have systems and methods for monitoring a vital sign for a person in a vehicle environment in a manner that does not require contact with that person. Having a contact-free system for monitoring vital signs ensures a comfortable traveling experience. The systems and methods described herein provide a contact-free way of monitoring at least one vital sign of a person with a desired level of accuracy. In particular, the embodiments described herein account for the noise that is inherent in the data generated by contactless sensors (e.g., surface displacement sensors) due to vibrations experienced in a vehicle environment. These vibrations may be due to various road conditions (e.g., road irregularities, road type, etc.), a body type of the person, a structural configuration of the seat in which the person is sitting, weather conditions, other factors, or a combination thereof.

In one or more example embodiments, movement data for a selected body location of a person in a vehicle is generated using a movement sensor positioned in the vehicle remotely with respect to the person. The movement sensor may be, for example, without limitation, mounted to the steering wheel or dashboard of the vehicle. Input data is formed for a machine learning system using the movement data. The input data is processed using the machine learning system to remove noise from the input data and generate a target output that identifies a vital sign of the person. The vital sign may be, for example, a heart rate, a respiration rate, or some other type of vital sign.

The machine learning system described above may be trained in various ways. In one or more example embodiments, this training includes receiving training data collected for a set of training scenarios. The training data includes measured vital sign data and sensor training data. The sensor training data includes surface displacement data that is generated remotely with respect to at least one person. Input data for the machine learning system is formed using the sensor training data. The machine learning system is trained using the input data to remove noise and generate a target output that corresponds with the measured vital sign data. The machine learning system described above may include, for example, without limitation, a neural network system. The neural network system may include one or more neural network models.

Thus, the systems and methods described herein provide a machine learning system (e.g., a neural network system) that is trained to remove noise due to vibrations in the vehicle environment for various scenarios. This machine learning system provides an easy and efficient way of monitoring vital signs while not detracting from the comfort and travel experience of persons in the vehicle. Further, the machine learning system enables the generation of a highly reliable target output identifying vital signs that has the desired level of accuracy needed to allow one or more actions to be taken based on the vital signs.

Figure 1:
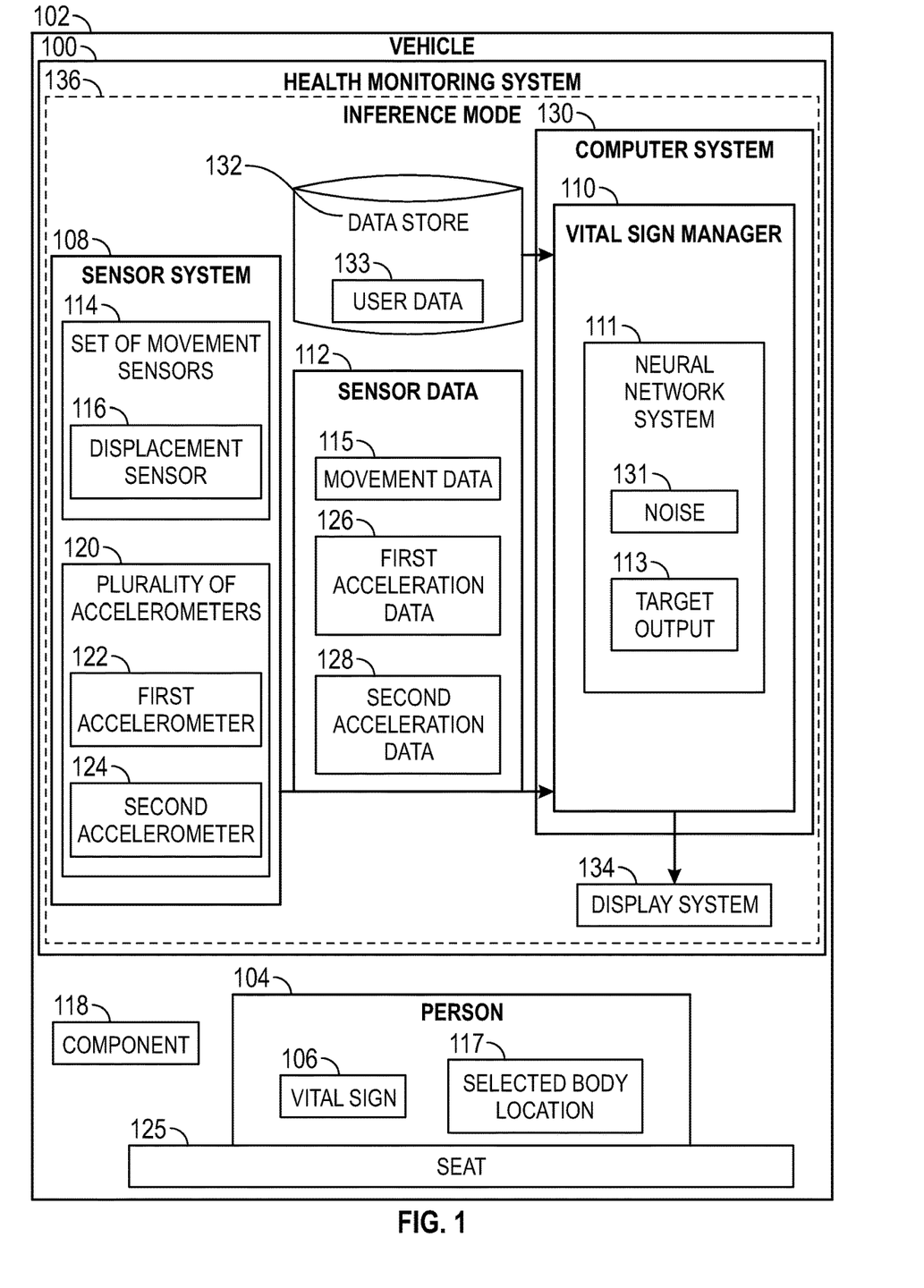
FIG. 1 is a block diagram of a health monitoring system in accordance with one or more embodiments.

Referring now to the figures, FIG. 1 is a block diagram of a health monitoring system 100 depicted in accordance with one or more embodiments. Health monitoring system 100 is used to monitor the health of one or more persons traveling within a vehicle, such as vehicle 102. For example, health monitoring system 100 may be used to monitor the health of person 104. Person 104 may be an operator (e.g., driver) of vehicle 102, a passenger of vehicle 102, or another type of user inside vehicle 102. Vehicle 102 may take a number of different forms. In one or more examples, vehicle 102 is an automobile (e.g., a car, a truck, etc.). In other examples, vehicle 102 may be some other type of ground vehicle (e.g., a train, a bus, a tractor, a loader, a bulldozer, an excavator, a crane operator, a tank, some other type of heavy-duty vehicle, etc.).

In particular, health monitoring system 100 may be used to monitor at least one vital sign 106 of person 104. A vital sign 106 may be a heart rate (or pulse rate), a respiratory rate, or some other type of vital sign that can be determined by measuring movement of a portion of the surface of the body (or body surface) of person 104. For example, heart rate may be determined by measuring displacement of the surface (e.g., skin) at a selected body location of person 104. The selected body location may be a location on the chest, the neck, the wrist, or some other portion of the body of person 104.

Health monitoring system 100 includes sensor system 108 and vital sign manager 110. Vital sign manager 110 uses a machine learning system to monitor one or more vital signs of one or more persons within vehicle 102 such as, for example, vital sign 106 of person 104. This machine learning system may include, for example, without limitation, neural network system 111. Neural network system 111 uses sensor data 112 generated by sensor system 108 to monitor vital sign 106. In particular, neural network system 111 is trained to process sensor data 112 and generate target output 113 that identifies the at least one vital sign 106 with a desired level of accuracy. Depending on the desired implementation, the desired level of accuracy may be, for example, but is not limited to, ≥90% accuracy, ≥95% accuracy, ≥98% accuracy, ≥99% accuracy, or another level of accuracy. Target output 113 may itself include the at least one vital sign 106 or may include data that can be further processed (e.g., scaled, etc.) to identify the at least one vital sign 106. For example, vital sign manager 110 may process target output 113 to extract vital sign 106.

Neural network system 111 includes one or more neural networks (or neural network models). A "neural network" (NN) refers to mathematical algorithms or computational models that mimic an interconnected group of artificial neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network processes information in two ways: via a training (or learning) mode and an inference (in-practice) mode. The neural network is in training mode when it is being trained to process training data and is in inference mode when it is putting what it has learned into practice. Neural networks may learn through a feedback process (e.g., backpropagation) which allows the neural network to adjust weight factors (e.g., modifying its behavior) of the individual nodes in the intermediate hidden layers so that the output corresponds with the outputs of the training data. In other words, it learns by being fed training data (learning examples) and eventually learns how to reach the desired or correct output, even when it is presented with a new range or set of inputs. Examples of various types of neural networks, include, but are not limited to: Feedforward Neural Network (FNN), Recurrent Neural Network (RNN), Modular Neural Network (MNN), Convolutional Neural Network (CNN), and Residual Neural Network (ResNet).

Sensor system 108 includes a plurality of sensors or devices for generating sensor data 112. As used herein, a "sensor" may comprise any number of sensors or devices. As used herein, sensor data 112 may refer to any portion of the data generated by one or more of the sensors that make up sensor system 108. In one or more embodiments, sensor system 108 includes set of movement sensors 114 that generate movement data 115. Set of movement sensors 114 includes one or more sensors that can operate as desired without making contact with person 104. In other words, each movement sensor in set of movement sensors 114 is a sensor that operates remotely (or contact-free) with respect to person 104.

In one or more embodiments, set of movement sensors 114 includes displacement sensor 116 that generates movement data 115 in the form of displacement data. Displacement sensor 116 may be used to measure, for example, surface displacement at selected body location 117 of person 104 in a remote (or contact-free) manner. Displacement sensor 116 may take the form of a radar sensor, a lidar sensor, a laser vibrometer (e.g., a laser doppler vibrometer), an ultrasound sensor, or another type of displacement sensor.

In one or more embodiments, displacement sensor 116 transmits a signal across a medium, which may be comprised of air and/or more objects (e.g., clothing) on person 104 or within vehicle 102, towards selected body location 117 of person 104 and receives a reflected signal back from the surface of selected body location 117 across the same medium that can be processed as sensor data 112. Selected body location 117 may include, for example, but is not limited to, a location on a neck, a location on a chest, a location on a another body part, or a combination thereof of person 104. In one or more examples, displacement sensor 116 is capable of measuring surface displacement at selected body location 117 in the sub-millimeter range.

In some embodiments, displacement sensor 116 is used to transmit a signal in a scanning pattern to enable surface displacement to be measured at multiple locations. For example, displacement sensor 116 may be moved in a scanning pattern that such the transmitted signal reaches and is reflected off of the surface of selected body location 117 of person 104 and another selected body location of another person (e.g., a passenger of vehicle 102).

At least one movement sensor of set of movement sensors 114 is positioned relative to component 118 of vehicle 102. As used herein, a first object (e.g., a movement sensor) being "positioned relative to" another a second object (e.g., component 118) means that the first item is positioned on, in, adjacent to, or near the second object. The first item may be positioned relative to the second object by being attached to, mounted to, welded to, embedded within a surface of, adhered to, embedded within, partially located inside of, or otherwise coupled to the second object.

Component 118 may be, for example, a steering wheel, a dashboard, a rearview mirror, a seat, a headrest, an inner portion of the roof of vehicle 102, or another part of vehicle 102. As one example, displacement sensor 116 may be positioned relative to component 118 such that displacement sensor 116 has a line of sight to selected body location 117. In one or more embodiments, component 118 is selected such that displacement sensor 116 has a line of sight to a similar selected body location of one or more other persons located in one or more different positions within vehicle 102. For example, displacement sensor 116 may be mounted (e.g., via a mounting or housing) to a rearview mirror of vehicle 102 such that displacement sensor 116 has a line of sight to the same selected body location on both a driver and a front passenger of vehicle 102.

In some embodiments, sensor system 108 further includes plurality of accelerometers 120 for measuring acceleration (e.g., vibrations). Plurality of accelerometers 120 includes at least first accelerometer 122 and second accelerometer 124. First accelerometer 122 and second accelerometer 124 are used to generate first acceleration data 126 and second acceleration data 128, respectively.

In one or more examples, first accelerometer 122 is positioned relative to one or more of set of movement sensors 114 such that first acceleration data 126 corresponds to the one or more of set of movement sensors 114. For example, first accelerometer 122 may be positioned relative to displacement sensor 116 (e.g., on a mount or housing physically associated with or otherwise coupled to displacement sensor 116) such that first acceleration data 126 measures acceleration (or vibrations) associated with displacement sensor 116.

In one or more examples, second accelerometer 124 is positioned in vehicle 102 to generate second acceleration data 128 that corresponds to vehicle 102. In other words, second acceleration data 128 measures acceleration (or vibrations) associated with vehicle 102 generally. As one example, second accelerometer 124 may be positioned relative to seat 125 in vehicle 102. For example, second accelerometer 124 may be positioned on a portion of seat 125 that makes contact with person 104 (e.g., the upper surface of a base of seat 125). In this example, second acceleration data 128 measures acceleration (or vibrations) associated with vehicle 102 by measuring the acceleration (or vibrations) associated with seat 125.

Vital sign manager 110 is communicatively coupled with sensor system 108. For example, vital sign manager 110 may receive sensor data 112 for processing using one or more communications links (e.g., wireless communications links, wired communications links, etc.). Vital sign manager 110 may be implemented using software, hardware, firmware, or a combination thereof. When software is used, the operations performed by vital sign manager 110 may be implemented using, for example, without limitation, program code configured to run on a processor unit. When firmware is used, the operations performed by vital sign manager 110 may be implemented using, for example, without limitation, program code and data and stored in persistent memory to run on a processor unit.

When hardware is employed, the hardware may include one or more circuits that operate to perform the operations performed by vital sign manager 110. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In one or more embodiments, vital sign manager 110 is implemented using computer system 130 onboard vehicle 102. Computer system 130 may include a single computer or multiple computers in communication with each other. Computer system 130 may be a vehicle computer system within vehicle 102 or may be communicatively coupled with the vehicle computer system. In one or more examples, computer system 130 is implemented entirely onboard vehicle 102. In other examples, computer system 130 is implemented partially onboard vehicle 102 and partially remotely with respect to vehicle 102. In still other examples, computer system 130 may be at least partially implemented within a cloud computing platform. Thus, although health monitoring system 100 is shown implemented onboard vehicle 102, in other embodiments, health monitoring system 100 may be at least partially implemented offboard or remotely with respect to vehicle 102. For example, one or more components of health monitoring system 100 may be implemented remotely.

Data store 132 may be communicatively coupled to computer system 130 or at least partially integrated as part of computer system 130. Data store 132 may be any hardware, firmware, and/or software implementation for storing data that vital sign manager 110 may use to monitor the at least one vital sign 106. For example, data store 132 may take the form of one or more databases, repositories, spreadsheets, servers, or a combination thereof.

Vital sign manager 110 uses neural network system 111 that has been trained to process sensor data 112 and remove noise 131 from sensor data 112 to generate target output 113 that identifies the at least one vital sign 106 for a person, such as person 104, with the desired level of accuracy. In some embodiments, sensor data 112 is preprocessed or transformed in some manner prior to being sent as input data into neural network system 111.

As one example, first acceleration data 126 and second acceleration data 128 may be processed to determine a relative motion of one or more of set of movement sensors 114 with respect to vehicle 102. This information may be used to filter movement data 115 prior to the data being sent into neural network system 111. In this manner, the filtered movement data forms the input data for neural network system 111. In other examples, movement data 115 is sent into neural network system 111 and a first neural network in neural network system 111 is used to filter movement data 115 to form input data for a second neural network in neural network system 111. This second neural network is trained to remove any additional noise 131 from the filtered movement data to generate target output 113.

In one or more embodiments, vital sign manager 110 uses user data 133 in data store 132 as reference for operation of the real-time vital sign monitoring. For example, neural network system 111 may include different neural network models tailored for different persons or users. For example, neural network system 111 may include one neural network for male users and another neural network for female users. In other examples, neural network system 111 may include one neural network for adults and another neural network for children.

In some cases, sensor system 108 includes one or more sensors (e.g., a pressure sensor, an imaging device, etc.) that generate data that can be compared with user data 133 to identify person 104 in some manner (e.g., male, female, adult, child, a specific person, etc.). User data 133 may also indicate which one or more neural networks in neural network system 111 to use to remove noise 131. In other examples, user data 133 may be used to identify data for initializing neural network system 111 based on an identification of person 104 (e.g., as male, female, adult, child, a specific person, etc.).

Noise 131 may be the result of vibrations of and inside vehicle 102. The magnitude of these vibrations may depend on, for example, without limitation, road conditions, vehicle speed, the body mass of person 104, structural characteristics of seat 125 in which person 104 is sitting, weather conditions (e.g., wind, rain, etc.), one or more other factors, or a combination thereof. Road conditions may factor in whether or not vehicle 102 is traveling on a residential street or a highway, whether the road is known to have potholes, bumps, or other irregularities, whether the road is a dirt, gravel, or concrete road, whether the road is above ground level, whether or one or more other conditions relating to the road are present, or a combination thereof. Structural characteristics of seat 125 may include, for example, characteristics of one or more springs in seat 125, characteristics of cushioning (e.g., foam) used in seat 125, one or more other structural characteristics, or a combination thereof. Noise 131 may be present across a wide frequency range and may occur with unpredictable intensity in different scenarios.

Once determined, vital sign 106 may be used in various ways. For example, health monitoring system 100 may monitor (e.g., track) vital sign 106 over time to determine whether a change occurs in vital sign 106 that requires medical attention. As another example, health monitoring system 100 may track vital sign 106 to determine whether vital sign 106 meets a set of criteria selected to determine whether or not one or more notifications (or alerts) are to be generated. For example, health monitoring system 100 may determine that an alert is to be generated and displayed to person 104 in response to a heart rate of person 104 falling below a selected threshold or rising above a selected threshold. In some cases, health monitoring system 100 sends vital sign 106 or information generated using vital sign 106 to a remote location (e.g., a cloud) for storage and/or further processing.

In some examples, vital sign 106 is used in conjunction with data from one or more other sensors to determine an emotional state of person 104. For example, vital sign 106 may be used to determine, validate, or corroborate a determination that person 104 is stressed, happy, or experiencing some other type of emotional state. Vital sign 106 may also be used for fitness tracking.

Vital sign 106 may also be used to control an operation of vehicle 102. For example, when vehicle 102 is a self-driving vehicle, vital sign manager 110 may determine whether vital sign 106 meets a set of criteria. If vital sign 106 meets that set of criteria, vital sign manager 110 may cause (e.g., send one or more commands that cause) vehicle 102 to travel to a medical facility (e.g., a clinic, a hospital, an urgent care center, etc.).

In one or more embodiments, health monitoring system 100 includes display system 134 communicatively coupled with computer system 130. In some embodiments, display system 134 is at least partially integrated within computer system 130. Display system 134 may include a set of display devices (e.g., a monitor, an LED display, a heads-up display, etc.). In one or more examples, health monitoring system 100 displays vital sign 106 using display system 134. In some examples, health monitoring system 100 uses vital sign 106 to generate an alert that is displayed on display system 134. In some examples, health monitoring system 100 uses vital sign 106 to generate information (e.g., a report on a general health of person 104) that is displayed on display system 134.

The description of health monitoring system 100 with respect to FIG. 1 corresponds to inference mode 136 for health monitoring system 100 (and thereby, for neural network system 111). Inference mode 136 may also be referred to as an in-practice mode.

The illustration of health monitoring system 100 in FIG. 1 is not meant to imply physical or architectural limitations to the manner in which one or more embodiments may be implemented. Other components in addition to or in place of the ones illustrated may be used. Some components may be optional. Additionally, one or more of the blocks may be presented to illustrate one or more functional components. In some cases, one or more of these blocks may be combined, divided, or combined and divided into different blocks.

As one example, while health monitoring system 100 is described above with respect to a machine learning system implemented using a deep learning system such as neural network system 111, one or more other types of machine learning systems may be used in addition to or in place of neural network system 111. For example, health monitoring system 100 may include a machine learning system that includes one or more reinforcement algorithms, one or more supervised learning algorithms, one or more unsupervised learning algorithms, or a combination thereof.

Figure 2:
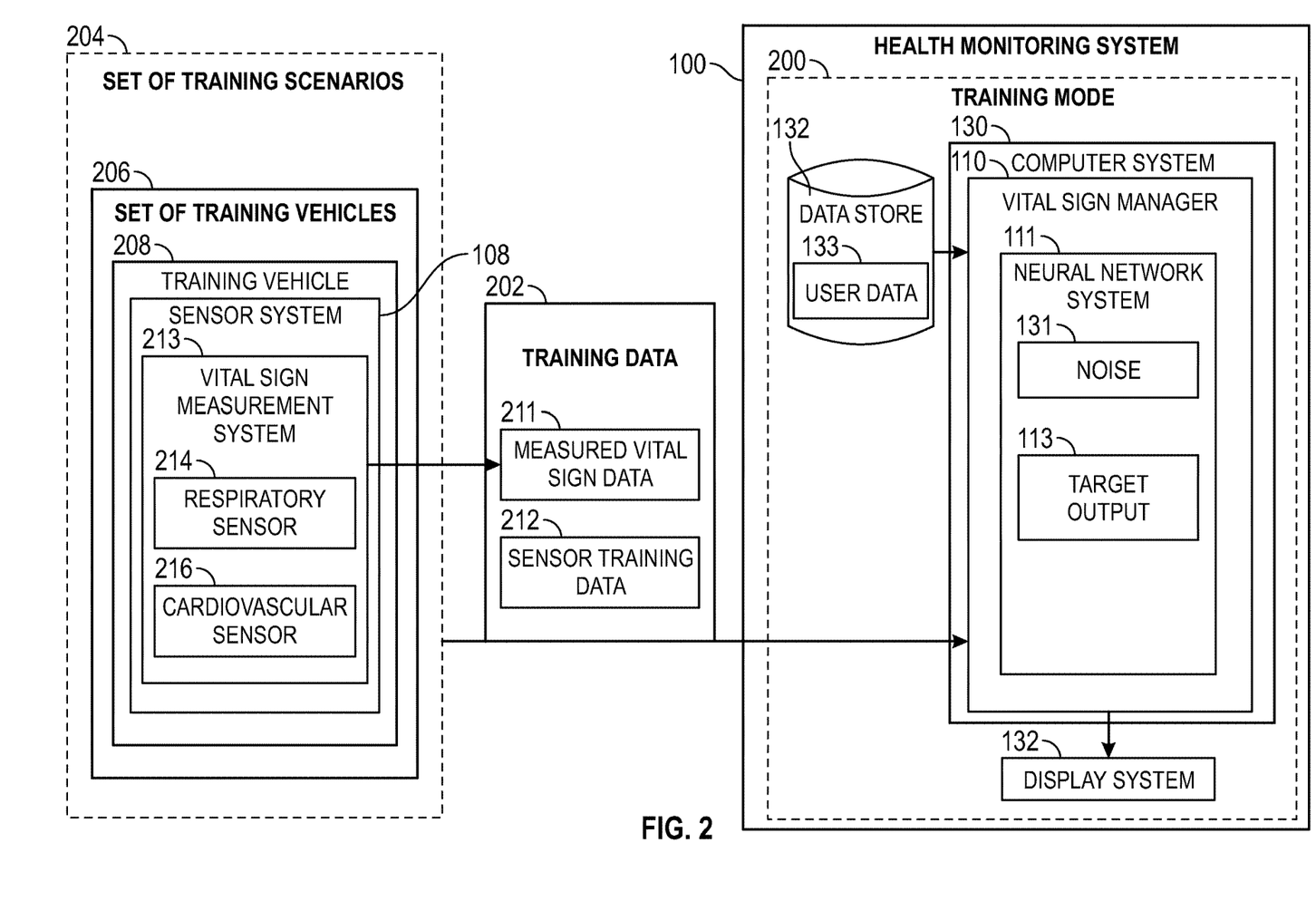
FIG. 2 is a block diagram of a health monitoring system in a training mode in accordance with one or more embodiments.

FIG. 2 is a block diagram of health monitoring system 100 from FIG. 1 being used in a training mode 200 in accordance with one or more embodiments. As described above, vital sign manager 110 of health monitoring system 100 includes neural network system 111. Training health monitoring system 100 includes training neural network system 111 using training data 202.

Training data 202 is collected over a set of training scenarios 204. In some cases, the training process is repeated for each training scenario of set of training scenarios 204 individually using training data 202 collected for that training scenario. In other cases, the training process is performed using the combined training data 202 collected for set of training scenarios 204. A "training scenario," such as one of set of training scenarios 204 may include one or more selected conditions or factors. For example, a training scenario may include a certain road condition(s), a vehicle speed profile (e.g., a single speed of travel, a profile of speed over a selected period of time), a type of vehicle, a type of seat in the vehicle, a body profile (e.g., a body mass of a person, a body type, and/or other body characteristics), a certain weather condition(s), one or more other factors, or a combination thereof.

In one or more examples, training is performed for set of training vehicles 206. In some examples, set of training vehicles 206 includes two or more different types of vehicles, two or more vehicles of the same type but with different seat types, or both. Training vehicle 208 is an example of one of set of training vehicles 206. In some examples, training vehicle 208 is also vehicle 102 from FIG. 1 in which health monitoring system 100 will be used in practice. In one or more examples, sensor system 108 from FIG. 1 may be used in each of the different vehicles of set of training vehicles 206 to generate sensor data that is used to form training data 202. In other examples, each of set of training vehicles 206 has a different sensor system implemented in a manner similar to sensor system 108 in FIG. 1 and the data from these various sensor systems is used to form training data 202.

Training data 202 includes measured vital sign data 211 and sensor training data 212. Measured vital sign data 211 may be generated by one or more sensors used for establishing "ground truth" data. As one example, sensor system 108 may include vital sign measurement system 213 that generates measured vital sign data 211. When health monitoring system 100 is being used in inference mode 136 as described above with respect to FIG. 1, vital sign measurement system 213 may be excluded from vehicle 102, deactivated (temporarily or permanently), or otherwise removed from use.

Vital sign measurement system 213 includes one or more sensors or devices that are wearable or meant to be operated in contact with a person. In other words, vital sign measurement system 213 may include, for example, one or more wearable devices (e.g., smartwatch capable of monitoring heart rate), one or more contact-based sensors, or a combination thereof. In some cases, vital sign measurement system 213 includes at least one sensor embedded in the steering wheel, seat, seatbelt, or another component of a vehicle.

In one or more embodiments, vital sign measurement system 213 includes respiratory sensor 214 and cardiovascular sensor 216. Respiratory sensor 214 may include, for example, a respiration belt or another type of device for measuring respiration rate. Cardiovascular sensor 216 may include, for example, an electrocardiogram (ECG) electrode for use in measuring heart rate. In this manner, measured vital sign data 211 may include measured respiration rate, measured heart rate, or both.

Sensor training data 212 includes data formed using the data from the one or more sensor systems implemented within set of training vehicles 206. These one or more sensor systems may include solely sensor system 108 and/or various sensor systems similar to sensor system 108. For example, sensor training data 212 may be formed using movement data 115 generated by set of movement sensors 114 from FIG. 1.

In some embodiments, sensor training data 212 may be formed using movement data 115 along with first acceleration data 126 and second acceleration data 128 generated by first accelerometer 122 and second accelerometer 124, respectively, from FIG. 1. For example, for training vehicle 208 that includes sensor system 108, first acceleration data 126 and second acceleration data 128 may be fused together or otherwise processed to determine the relative motion of set of movement sensors 114 with respect to training vehicle 208 (or vice versa, the relative motion of training vehicle 208 with respect to set of movement sensors 114).

First acceleration data 126 and second acceleration data 128 enable vital sign manager 110 to deterministically remove or filter out vibrations from movement data 115 based on an understanding of the motion of set of movement sensors 114 relative to training vehicle 208. This type of processing may also provide an understanding of skin displacement relative to the rest of the body of a person when a vehicle is moving. The filtering described above may occur outside of neural network system 111 prior to sensor training data 212 being sent into neural network system 111 or may occur within neural network system 111.

Training neural network system 111 as described above enables neural network system 111 to generate target output 113 that identifies a vital sign (such as vital sign 106 of person 104 in FIG. 1) with a desired level of accuracy. The more robust that training data 202 is, the more accurate and precise that target output 113 is.

Figure 3:
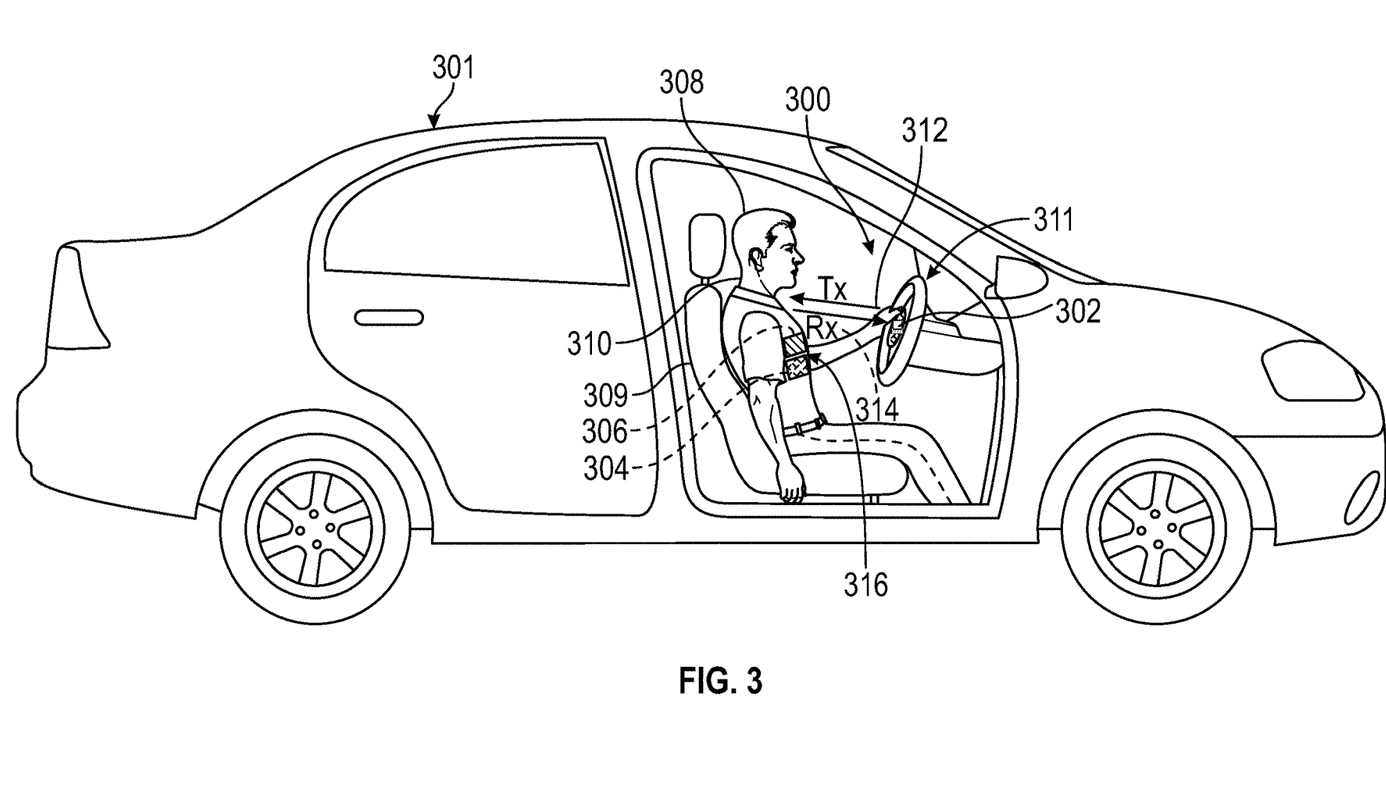
FIG. 3 is a training setup for a health monitoring system in accordance with one or more embodiments.

FIG. 3 is an illustration of a training setup for a health monitoring system inside a vehicle in accordance with one or more embodiments. Health monitoring system 300 is an example of one implementation for health monitoring system 100 described in FIGS. 1 and 2. Health monitoring system 300 is shown in a training mode within vehicle 301.

In this example, health monitoring system 300 includes displacement sensor 302, respiratory sensor 304, and cardiovascular sensor 306, which may be examples of implementations for displacement sensor 116, respiratory sensor 214, and cardiovascular sensor 216, respectively, from FIGS. 1-2. Respiratory sensor 304 and cardiovascular sensor 306 are positioned relative to person 308 (an example of person 104 in FIG. 1) who is sitting in seat 309. Seat 309 is an example of one implementation for seat 125 in FIG. 1. Displacement sensor 302 is positioned in vehicle 301 remotely with respect to person 308.

Displacement sensor 302 may be a radar sensor, a lidar sensor, an ultrasound sensor, a laser vibrometer, or some other type of sensor for measuring displacement. In this example, displacement sensor 302 is positioned away from (e.g., at a distance from so as to not have contact with) neck 310 of person 308 such that displacement sensor 302 has a line of sight to neck 310. In particular, displacement sensor 302 is contact-free (or contactless) with respect to its contact with person 308. In this example, displacement sensor 302 is positioned relative to steering wheel 311. In particular, displacement sensor 302 is mounted to steering wheel 311. Displacement sensor 302 transmits a signal 312 towards neck 310 and receives reflected signal 314 back. In some examples, displacement sensor 302 is capable of transmitting and receiving in a scanning pattern to capture displacement at other locations (e.g., the neck of another person sitting in a different seat inside vehicle 301).

Respiratory sensor 304 takes the form of a respiratory belt in this example. Further, cardiovascular sensor 306 takes the form of an ECG electrode in this example. Respiratory sensor 304 and cardiovascular sensor 306 are positioned in contact with chest 316 of person 308. The measured vital sign data generated by respiratory sensor 304 and cardiovascular sensor 306 may be sufficiently accurate and precise such that the measured vital sign data can be used as "ground truth" data for training.

Figure 4:
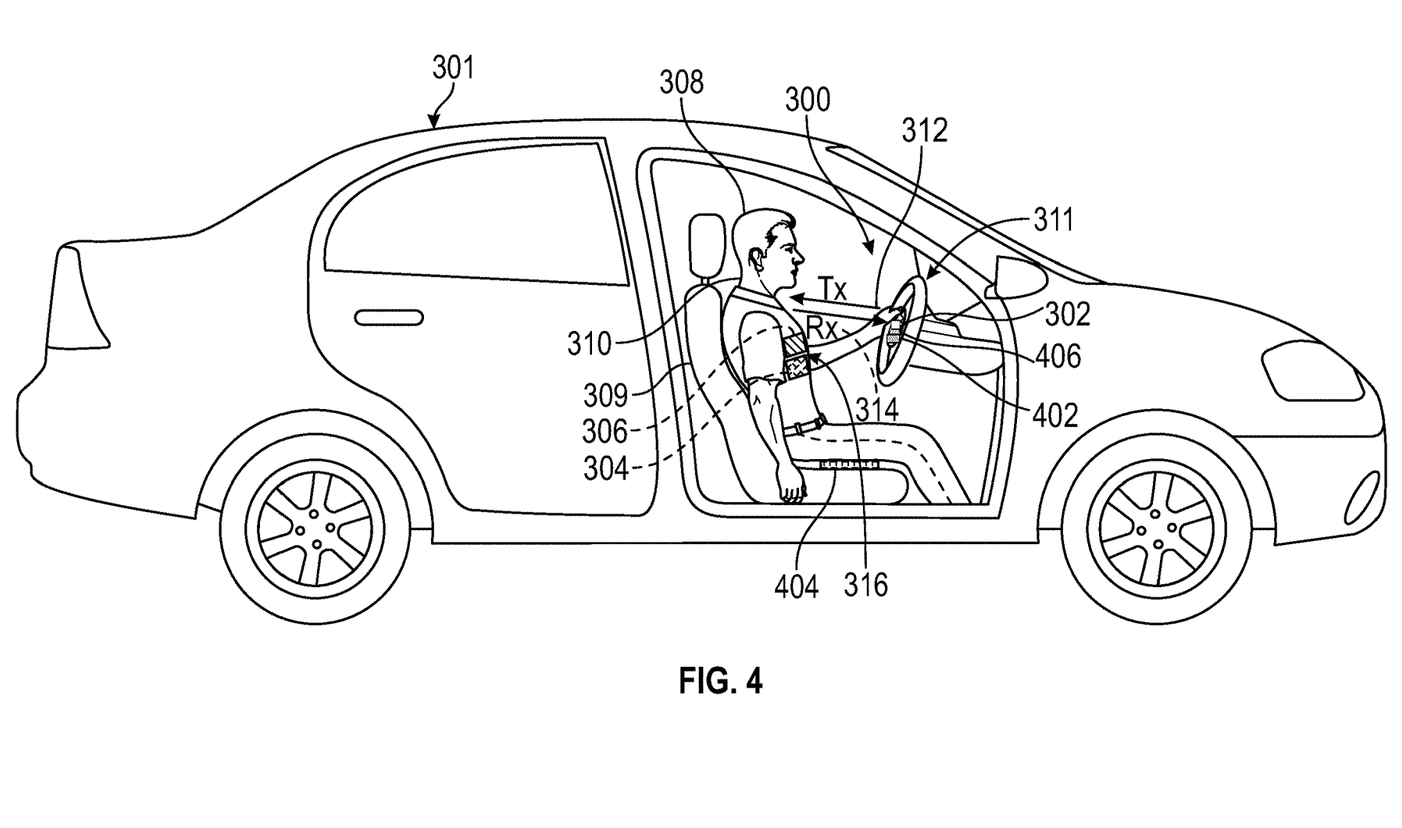
FIG. 4 is a different training setup for the health monitoring system of FIG. 3 in accordance with one or more embodiments.

FIG. 4 is an illustration of a different training setup for health monitoring system 300 inside vehicle 301 in accordance with one or more embodiments. In this example, health monitoring system 300 includes first accelerometer 402 and second accelerometer 404, which may be examples of implementations for first accelerometer 122 and second accelerometer 124, respectively, from FIG. 1.

First accelerometer 402 is positioned relative to displacement sensor 302. For example, displacement sensor 302 may be attached to steering wheel 311 via mount (or housing) 406. In this example, first accelerometer 402 is positioned on mount (or housing) 406. Second accelerometer 404 is positioned relative to seat 309. In one or more examples, second accelerometer 404 is positioned on seat 309 beneath person 308. The first acceleration data generated by first accelerometer 402 and the second acceleration data generated by second accelerometer 404 are processed together (e.g., fused) to measure motion of displacement sensor 302 (or the displacement of neck 310) relative to the motion of seat 309 (or the displacement of the rest of the body of person 308).

Figure 5:
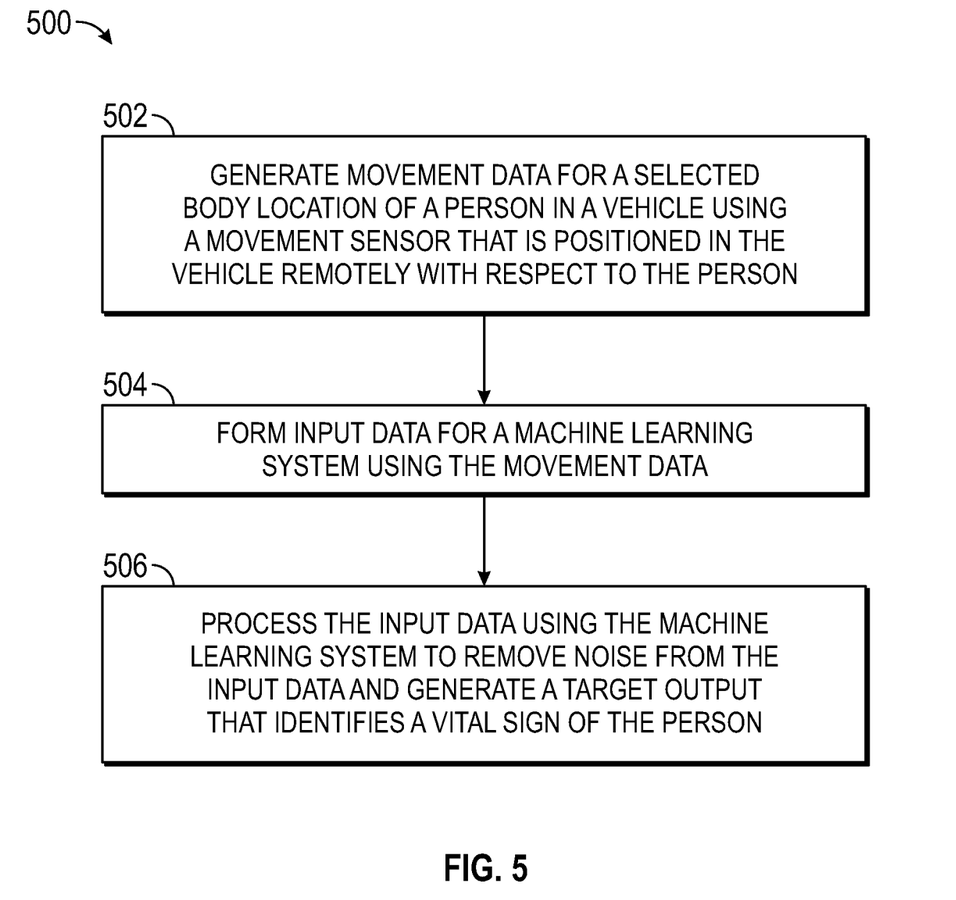
FIG. 5 is a flowchart of a method for monitoring a vital sign in accordance with one or more embodiments.

FIG. 5 is a flowchart of a method 500 for monitoring a vital sign in accordance with one or more embodiments. Method 500 is illustrated as a set of operations or steps and is described with continuing reference to FIGS. 1-2. One or more operations or steps that are not expressly illustrated in FIG. 5 may be included before, after, in between, or as part of the operations or steps of method 500. In some embodiments, one or more of the operations or steps may be implemented, at least in part, in the form of executable code stored on non-transitory, tangible, machine-readable media that when run by one or more processors may cause the one or more processors to perform one or more of the processes. Method 500 may be implemented using health monitoring system 100 described in FIGS. 1-2.

Method 500 may begin by generating movement data for a selected body location of a person in a vehicle using a movement sensor that is positioned in the vehicle remotely with respect to the person (step 502). The movement sensor may take the form of, for example, a displacement sensor such as displacement sensor 116 in FIG. 1. The movement sensor is positioned in the vehicle such that it is contact-free. In other words, the movement sensor is spaced apart from or at a distance from the person. In one or more examples, the movement sensor is positioned on a steering wheel, a dashboard, a rearview mirror, a seat, a headrest, an inner portion of the roof of vehicle 102, or another part of the vehicle.

The movement data is used to form input data for a machine learning system (step 504). In one or more examples, the machine learning system includes a neural network system such as neural network system 111 in FIG. 1. In some examples, step 504 includes sending the movement data as input data directly into the neural network system. In other examples, step 504 includes preprocessing the movement data prior to sending it as input data to the neural network system. For example, the movement data may be normalized, scaled, filtered, or processed in some other manner prior to forming the input data for the neural network system. The neural network system may be, for example, neural network system 111 described in FIGS. 1-2.

The input data is processed using the machine learning system to remove noise from the input data and generate a target output that identifies a vital sign of the person (step 506). The machine learning system (e.g., neural network system) described in step 506 is one that has been previously trained across a set of training scenarios to remove noise from the input data to generate the target output. This noise may be due to, for example, without limitation, road conditions (e.g., road irregularities and bumps), a type of roadway, a vehicle type, a speed of the vehicle, a body mass of the person, a body type of the person, weather conditions, other factors, or a combination thereof.

Figure 6:
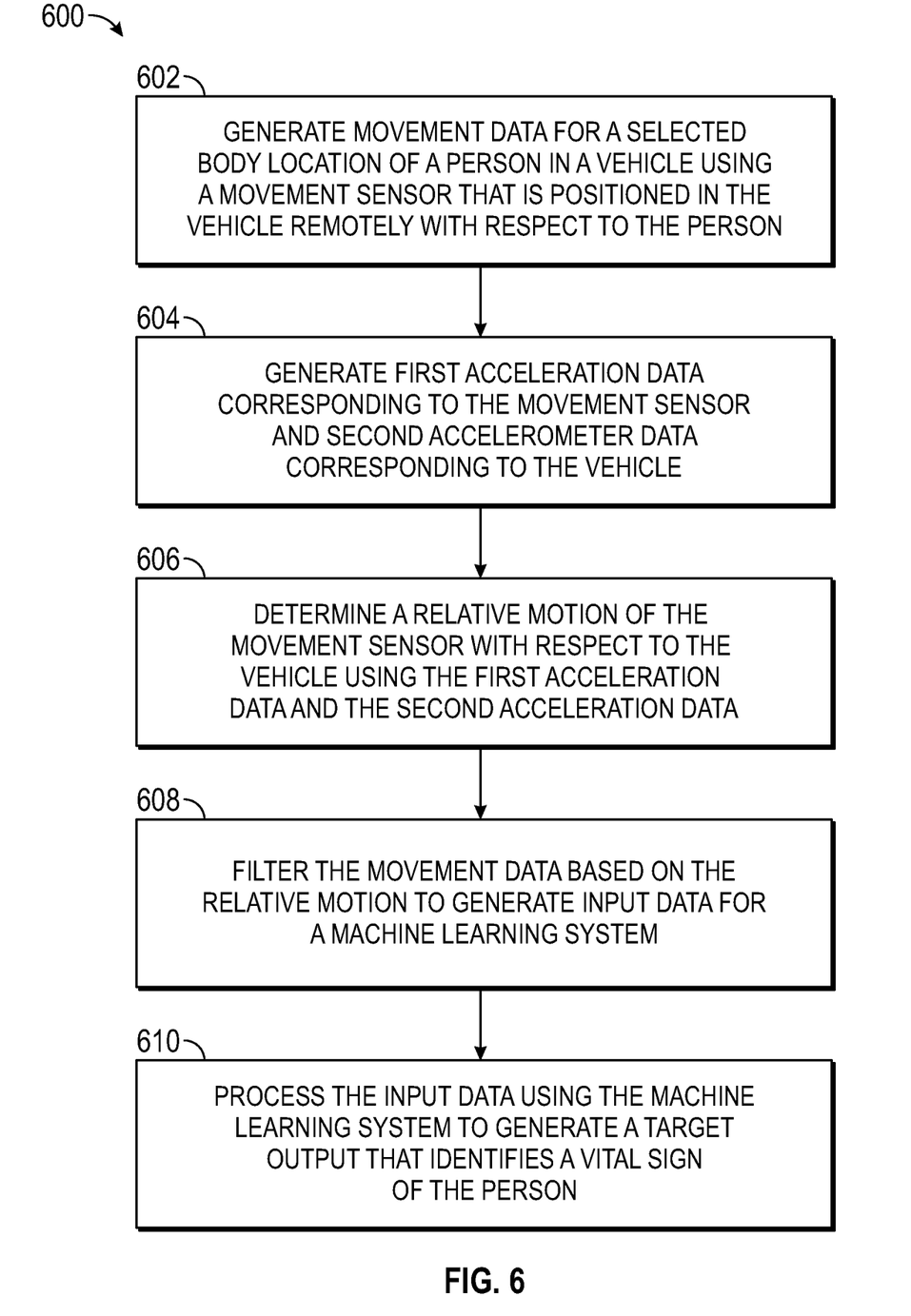
FIG. 6 is a flowchart of a method for monitoring a vital sign in accordance with one or more embodiments.

FIG. 6 is a flowchart of a different method 600 for monitoring a vital sign in accordance with one or more embodiments. Method 600 is illustrated as a set of operations or steps and is described with continuing reference to FIGS. 1-2. One or more operations or steps that are not expressly illustrated in FIG. 6 may be included before, after, in between, or as part of the operations or steps of method 600. In some embodiments, one or more of the operations or steps may be implemented, at least in part, in the form of executable code stored on non-transitory, tangible, machine-readable media that when run by one or more processors may cause the one or more processors to perform one or more of the processes. Method 600 may be implemented using health monitoring system 100 described in FIGS. 1-2.

Method 600 begins by generating movement data for a selected body location of a person in a vehicle using a movement sensor that is positioned in the vehicle remotely with respect to the person (step 602). First acceleration data corresponding to the movement sensor and second acceleration data corresponding to the vehicle are generated (step 604). This acceleration data may be generated using accelerometers such as, for example, first accelerometer 122 and second accelerometer 124 in FIG. 1.

A relative motion of the movement sensor with respect to the vehicle is determined using the first acceleration data and the second acceleration data (step 606). Understanding this relative motion provides an understanding of the extent of the impact of the motion of the vehicle on the movement data generated by the movement sensor. The movement data is filtered based on the relative motion to generate input data for a machine learning system (step 608). The input data is processed using the machine learning system to remove noise and generate a target output that identifies a vital sign of the person (step 610).

The machine learning system described above may include any number of or combination of reinforcement algorithms, supervised learning algorithms, unsupervised learning algorithms. In one or more examples, the machine learning system includes a deep learning system (e.g., a neural network system) that may be comprised of one or more deep learning algorithms or models.

Figure 7:
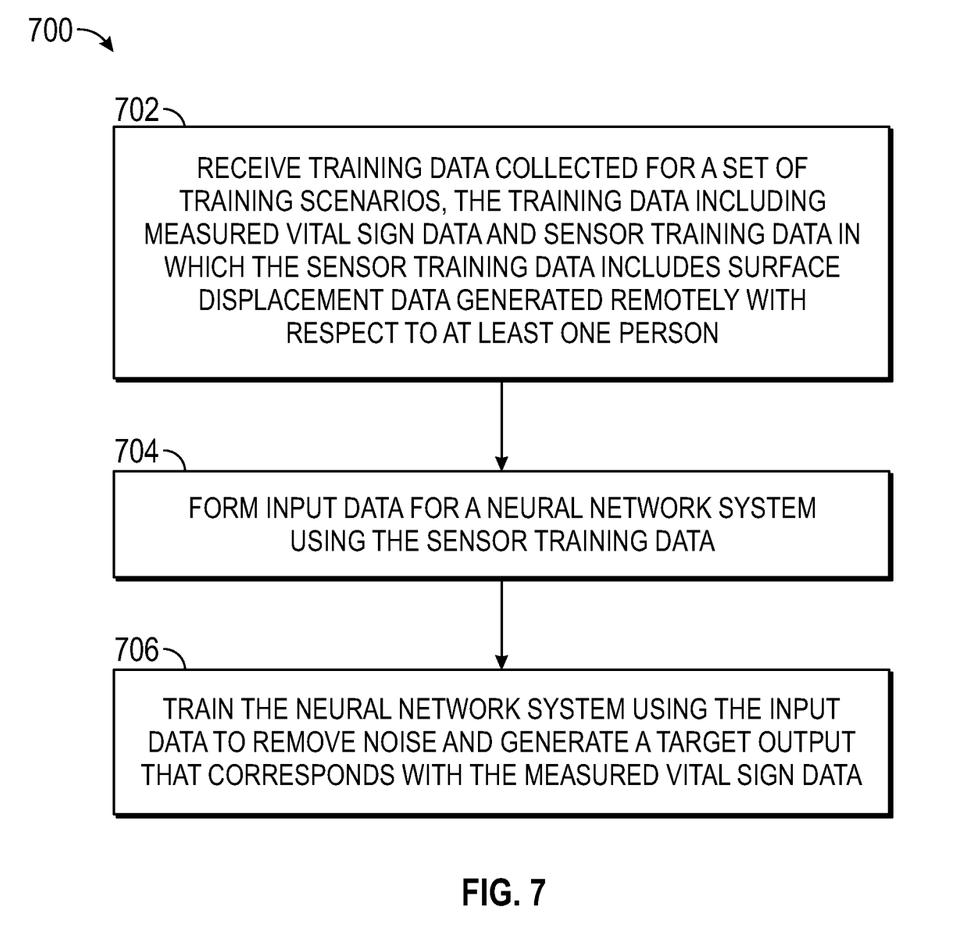
FIG. 7 is a flowchart of a method for training a neural network system to monitor a vital sign in accordance with one or more embodiments.

FIG. 7 is a flowchart of a method 700 for training a neural network system to monitor a vital sign in accordance with one or more embodiments. Method 700 is illustrated as a set of operations or steps and is described with continuing reference to FIGS. 1-2. One or more operations or steps that are not expressly illustrated in FIG. 7 may be included before, after, in between, or as part of the operations or steps of method 700. In some embodiments, one or more of the operations or steps may be implemented, at least in part, in the form of executable code stored on non-transitory, tangible, machine-readable media that when run by one or more processors may cause the one or more processors to perform one or more of the processes. Method 700 may be implemented using health monitoring system 100 described in FIGS. 1-2.

Method 700 begins by receiving training data collected for a set of training scenarios, the training data including measured vital sign data and sensor training data (step 702). In some embodiments, the set of training scenarios includes training scenarios that vary by at least one factor. The at least one factor may include, for example, a certain road condition(s), a vehicle speed profile (e.g., a single speed of travel, a profile of speed over a selected period of time), a type of vehicle, a type of seat in the vehicle, a body profile (e.g., a body mass of a person, a body type, and/or other body characteristics), a certain weather condition(s), one or more other factors, or a combination thereof.

This set of training scenarios may correspond to a set of training vehicles. For example, training data for two training scenarios may be collected for a first training vehicle, while training data for four training scenarios may be collected for a second training vehicle. The second training vehicle may be a same type or a different type than the first training vehicle. In some embodiments, the first training vehicle and the second training vehicle may be the same type of vehicle but with different structural configurations. In other embodiments, the first training vehicle and the second training vehicle are different models of vehicles.

As described above, the training data received in step 702 includes measured vital sign data and sensor training data. The measured vital sign data may be generated by a vital sign measurement system such as vital sign measurement system 213 in FIG. 2. In particular, the measured vital sign data may be generated by one or more sensors that measure one or more vital signs (e.g., heart rate, respiratory rate) via contact with a person. This measured vital sign data serves as "ground truth" data for a neural network system. The sensor training data includes data generated by sensor systems (e.g., similar to sensor system 108 described in FIGS. 1-2) installed on the set of training vehicles. In some examples, the same sensor system may be used for collecting data from each of the set of training vehicles for each of the set of training scenarios. In other examples, each training vehicle in the set of training vehicles may have a different sensor system, but these various sensor systems may be implemented similarly (e.g., include the same types of sensors).

The sensor training data is used to form input data for a neural network system (step 704). In some embodiments, step 704 includes sending the sensor training data into the neural network system directly as the input data. In other embodiments, step 704 includes preprocessing the sensor training data. For example, the sensor training data may be normalized, scaled, filtered, or processed in some other manner prior to forming the input data for the neural network system.

In yet other embodiments, the sensor training data may undergo an initial filtering for noise based on acceleration data. For example, the sensor training data may include displacement data as well as acceleration data from a plurality of accelerometers. The acceleration data may be used to provide information about the relative motion of the one or more displacement sensors that generated the displacement data with respect to the training vehicle(s) in which the one or more displacement sensors are used. This information is used to perform an initial filtering out of noise in the displacement data to form the input data.

The neural network system is trained using the input data to remove noise and generate a target output that corresponds with the measured vital sign data (step 706). In one or more examples, the neural network system may include one or more neural networks that are trained on the input data to generate a target output that matches the measured vital sign data within selected tolerances (e.g., a desired level of accuracy).

The flowcharts and block diagrams in the different depicted embodiments illustrate the architecture, functionality, and operation of some possible implementations of apparatuses and methods in an embodiment. In this regard, each block in the flowcharts or block diagrams may represent a module, a segment, a function, and/or a portion of an operation or step. In some alternative implementations of an embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 8:
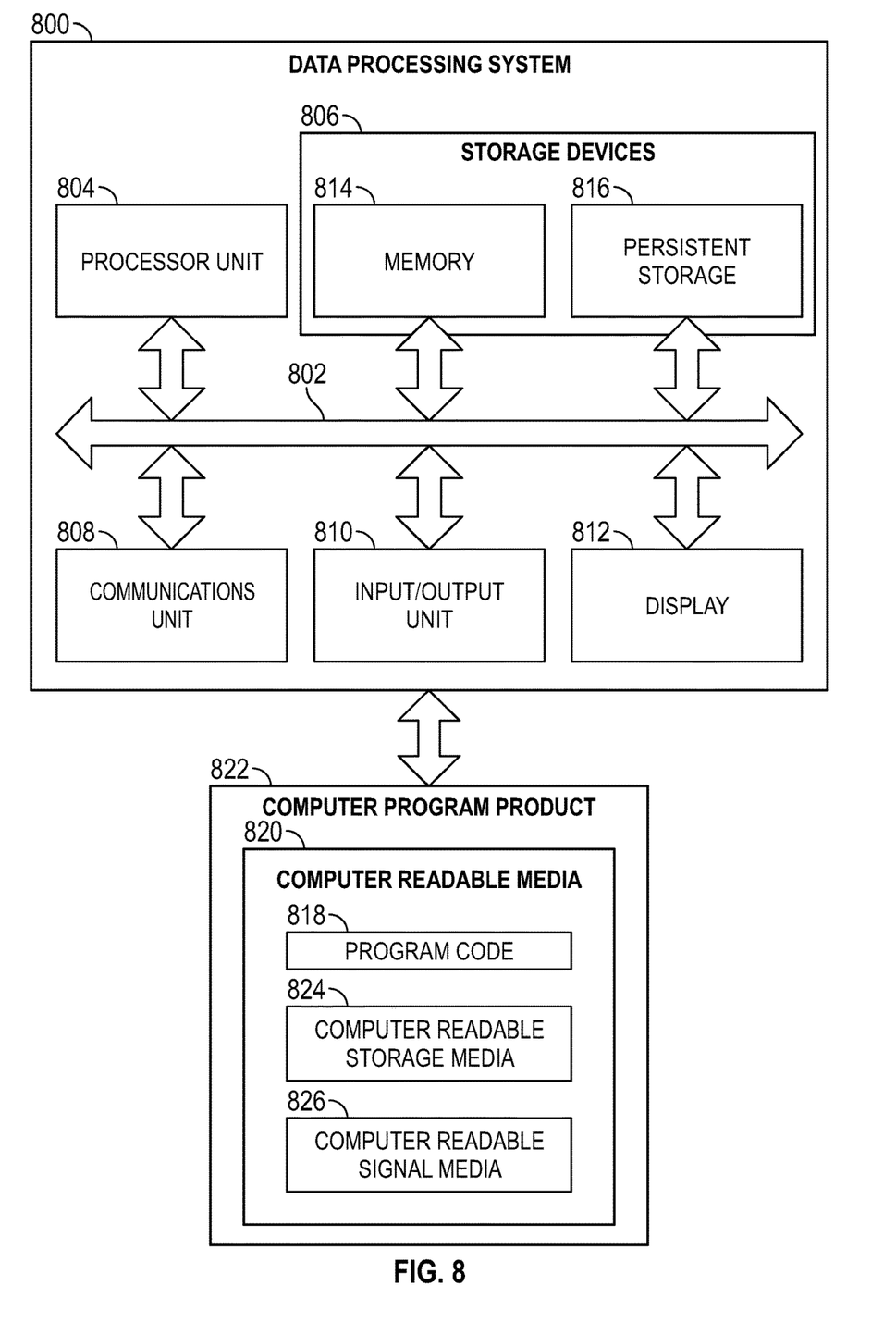
FIG. 8 is a block diagram of a data processing system in accordance with one or more embodiments.

FIG. 8 is a block diagram of a data processing system in accordance with one or more embodiments. Data processing system 800 is an example one manner in which computer system 130 in FIG. 1 may be implemented. As depicted, data processing system 800 includes communications framework 802, which provides communications between processor unit 804, storage devices 806, communications unit 808, input/output unit 810, and display 812. In some cases, communications framework 802 may be implemented as a bus system.

Processor unit 804 is configured to execute instructions for software to perform a number of operations. Processor unit 804 may comprise a number of processors, a multi-processor core, and/or some other type of processor, depending on the implementation. In some cases, processor unit 804 may take the form of a hardware unit, such as a circuit system, an application specific integrated circuit (ASIC), a programmable logic device, or some other suitable type of hardware unit.

Instructions for the operating system, applications, and/or programs run by processor unit 804 may be located in storage devices 806. Storage devices 806 may be in communication with processor unit 804 through communications framework 802. As used herein, a storage device, also referred to as a computer readable storage device, is any piece of hardware capable of storing information on a temporary and/or permanent basis. This information may include, but is not limited to, data, program code, and/or other information.

Memory 814 and persistent storage 816 are examples of storage devices 806. Memory 814 may take the form of, for example, a random access memory or some type of volatile or non-volatile storage device. Persistent storage 816 may comprise any number of components or devices. For example, persistent storage 816 may comprise a hard drive, a solid state drive, a flash memory, a rewritable optical disk, a rewritable magnetic tape, or some combination of the above. The media used by persistent storage 816 may or may not be removable.

Communications unit 808 allows data processing system 800 to communicate with other data processing systems and/or devices. Communications unit 808 may provide communications using physical and/or wireless communications links.

Input/output unit 810 allows input to be received from and output to be sent to other devices connected to data processing system 800. For example, input/output unit 810 may allow user input to be received through a keyboard, a mouse, and/or some other type of input device. As another example, input/output unit 810 may allow output to be sent to a printer connected to data processing system 800.

Display 812 is configured to display information to a user. Display 812 may comprise, for example, without limitation, a monitor, a touch screen, a laser display, a holographic display, a virtual display device, and/or some other type of display device.

In this illustrative example, the processes of the different illustrative embodiments may be performed by processor unit 804 using computer-implemented instructions. These instructions may be referred to as program code, computer usable program code, or computer readable program code and may be read and executed by one or more processors in processor unit 804.

In these examples, program code 818 is located in a functional form on computer readable media 820, which is selectively removable, and may be loaded onto or transferred to data processing system 800 for execution by processor unit 804. Program code 818 and computer readable media 820 together form computer program product 822. In this illustrative example, computer readable media 820 may be non-transitory (e.g., computer readable storage media 824) or transitory (e.g., computer readable signal media 826).

Computer readable storage media 824 is a physical or tangible storage device used to store program code 818 rather than a medium that propagates or transmits program code 818. Computer readable storage media 824 may be, for example, without limitation, an optical or magnetic disk or a persistent storage device that is connected to data processing system 800.

Alternatively, program code 818 may be transferred to data processing system 800 using computer readable signal media 826. Computer readable signal media 826 may be, for example, a propagated data signal containing program code 818. This data signal may be an electromagnetic signal, an optical signal, and/or some other type of signal that can be transmitted over physical and/or wireless communications links.

The illustration of data processing system 800 in FIG. 8 is not meant to provide architectural limitations to the manner in which the illustrative embodiments may be implemented. The different illustrative embodiments may be implemented in a data processing system that includes components in addition to or in place of those illustrated for data processing system 800. Further, components shown in FIG. 8 may vary from the illustrative examples shown.

The present embodiments can take the form of an entirely hardware embodiment, an entirely software embodiment, or an embodiment containing both hardware and software elements. Accordingly, it is understood that any operation of the computing systems may be implemented by a computing system using corresponding instructions stored on or in a non-transitory computer readable medium accessible by a processing system. For the purposes of this description, a tangible computer-usable or computer-readable medium can be any apparatus that can store the program for use by or in connection with the instruction execution system, apparatus, or device. The medium may include non-volatile memory including magnetic storage, solid-state storage, optical storage, cache memory, and RAM.

As used herein, the phrase "at least one of" when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" or "at least one of item A, item B, and item C" may mean item A; item A and item B; item B; item A, item B, and item C; item B and item C; or item A and C. In some cases, "at least one of item A, item B, or item C" or "at least one of item A, item B, and item C" may mean, but is not limited to, two of item A, one of item B, and ten of item C; four of item B and seven of item C; or some other suitable combination.

While certain exemplary embodiments of the invention have been described and shown in the accompanying drawings, it is to be understood that such embodiments are merely illustrative of and not restrictive on the broad invention, and that the embodiments of the invention are not limited to the specific constructions and arrangements shown and described, since various other modifications may occur to those ordinarily skilled in the art. The intention is to cover all modifications, equivalents and alternatives falling within the spirit and scope of the disclosure as defined by the claims.

What is claimed is:

1. A system comprising:
   a movement sensor positioned in a vehicle for remotely measuring movement of a selected body location of a person to generate movement data,
     wherein the movement sensor is positioned away from the person such that the movement sensor is contactless with respect to the person; and
   a vital sign manager that forms input data for a machine learning system using the movement data and processes the input data using the machine learning system to remove noise from the input data and generate a target output that identifies a vital sign of the person,
     wherein the vital sign manager forms the input data based on a relative motion of the movement sensor with respect to the vehicle, the relative motion being determined using first acceleration data corresponding to a first acceleration of the movement sensor and second acceleration data corresponding to a second acceleration of the vehicle, wherein the first acceleration of the movement sensor is independent of the movement of the selected body location of the person.

2. The system of claim 1, further comprising:
a plurality of accelerometers for generating the first acceleration data corresponding to the movement sensor and the second accelerometer data corresponding to the vehicle.

3. The system of claim 2, wherein the vital sign manager determines the relative motion of the movement sensor with respect to the vehicle using the first acceleration data and the second acceleration data and filters the movement data based on the relative motion to reduce an impact of the movement of the vehicle on the movement data used to generate the input data.

4. The system of claim 2, wherein the plurality of accelerometers comprises:
a first accelerometer positioned relative to the movement sensor; and
a second accelerometer positioned inside the vehicle.

5. The system of claim 2, wherein the plurality of accelerometers comprises:
a first accelerometer positioned on a mount that attaches the movement sensor to a component of the vehicle; and
a second accelerometer positioned on a seat in the vehicle.

6. The system of claim 1, wherein the movement sensor comprises at least one displacement sensor selected from a group consisting of a radar sensor, a lidar sensor, a laser vibrometer, and an ultrasound sensor.

7. The system of claim 1, wherein the movement sensor is mounted to a component in the vehicle selected from a group consisting of a steering wheel, a rearview mirror, and a headrest.

8. The system of claim 1, wherein the machine learning system is trained to remove the noise from the input data based on sensor training data and measured vital sign data generated by at least one of a respiratory sensor or a cardiovascular sensor in contact with the person.

9. The system of claim 1, wherein the vital sign manager generates an alert in response to the vital sign meeting a set of criteria.

10. The system of claim 1, wherein the machine learning system is trained using training data collected over a set of training scenarios to remove the noise from the input data, and wherein a training scenario in the set of training scenarios includes at least one of a road condition, a vehicle speed profile, a type of vehicle, a type of seat, a body profile, or a weather condition.

11. The system of claim 1, wherein the vital sign is heart rate, the movement sensor is a displacement sensor, and the selected body location comprises at least one of a first location on a surface of a neck or a second location on a surface of a chest.

12. The system of claim 1, wherein the movement sensor is positioned to allow scanning multiple locations using a signal transmitted by the movement sensor.

13. A method comprising:
generating movement data for a selected body location of a person in a vehicle using a movement sensor that remotely measures movement of the selected body location of the person, wherein the movement sensor is positioned in the vehicle away from the person such that the movement sensor is contactless with respect to the person;
measuring a first acceleration of the movement sensor to generate first acceleration data, wherein the first acceleration of the movement sensor is independent of the movement of the selected body location of the person;
measuring a second acceleration of the vehicle to generate second acceleration data;
determining a relative motion of the movement sensor with respect to the vehicle using the first acceleration data and the second acceleration data;
filtering the movement data for the selected body location of the person based on the determined relative motion to form input data for a machine learning system; and
processing the input data using the machine learning system to remove noise from the input data and generate a target output that identifies a vital sign of the person.

14. The method of claim 13,
wherein the movement sensor includes a displacement sensor having a line of sight to the selected body location of the person.

15. The method of claim 14, wherein forming the input data comprises:
filtering the movement data based on the relative motion to reduce an impact of the acceleration of the vehicle on the movement data of the selected body location of the person used to generate the input data.

16. The method of claim 13, wherein generating the movement data comprises:
generating surface displacement data using a displacement sensor that includes at least one of a radar sensor, a lidar sensor, a laser vibrometer, or an ultrasound sensor.

17. The method of claim 13, wherein processing the input data comprises:
removing the noise from the input data, the noise being due to at least one of a road condition, a weather condition, a body type, or a vehicle speed.

18. The method of claim 13, further comprising:
training the machine learning system to remove the noise based on training data collected for a set of training scenarios, the training data including sensor training data and measured vital sign data.

19. The method of claim 13, further comprising:
determining whether the vital sign meets a set of criteria; and
generating an alert in response to the vital sign meeting the set of criteria.

20. A method comprising:
receiving training data collected for a set of training scenarios, the training data including measured vital sign data, sensor training data, first acceleration data, and second acceleration data,
wherein the sensor training data includes surface displacement data that is generated by remotely measuring surface displacement for at least one person using one or more sensor systems positioned contactless with respect to the at least one person in a set of training vehicles,
wherein the first acceleration data is generated based on measuring first acceleration for the one or more sensor systems, the first acceleration being independent of the surface displacement for the at least one person, and wherein the second acceleration data is generated based on measuring second acceleration for the set of training vehicles;
filtering out initial noise from the surface displacement data based on the first acceleration data and the second acceleration data to form filtered surface displacement data;
forming input data for a neural network system using the sensor training data that includes the filtered surface displacement data; and
training the neural network system using the input data to remove noise and generate a target output that corresponds with the measured vital sign data.

* * * * *